(12) United States Patent
Wong et al.

(10) Patent No.: US 9,566,414 B2
(45) Date of Patent: Feb. 14, 2017

(54) INTEGRATED CATHETER AND GUIDE WIRE CONTROLLER

(71) Applicant: Hansen Medical, Inc., Mountain View, CA (US)

(72) Inventors: Serena H. Wong, Mountain View, CA (US); Sean Paul Walker, Fremont, CA (US); June Park, Palo Alto, CA (US); Richard Henderson, Fremont, CA (US)

(73) Assignee: HANSEN MEDICAL, INC., Moutain View, CA (US)

( * ) Notice: Subject to any disclaimer, the term of this patent is extended or adjusted under 35 U.S.C. 154(b) by 292 days.

(21) Appl. No.: 13/800,261

(22) Filed: Mar. 13, 2013

(65) Prior Publication Data
US 2014/0276646 A1 Sep. 18, 2014

(51) Int. Cl.
*A61B 34/00* (2016.01)
*A61B 34/30* (2016.01)
*A61M 25/01* (2006.01)

(52) U.S. Cl.
CPC .......... *A61M 25/0105* (2013.01); *A61B 34/30* (2016.02); *A61B 34/74* (2016.02); *A61B 2034/301* (2016.02); *A61B 2034/742* (2016.02)

(58) Field of Classification Search
CPC ................................................. A61M 25/0105
See application file for complete search history.

(56) References Cited

U.S. PATENT DOCUMENTS

| 5,366,444 A | 11/1994 | Martin |
| 5,398,691 A | 3/1995 | Martin et al. |
| 5,408,409 A | 4/1995 | Glassman et al. |
| 5,499,632 A * | 3/1996 | Hill et al. ...................... 600/585 |
| 5,524,180 A | 6/1996 | Wang et al. |
| 5,631,973 A | 5/1997 | Green |
| 5,713,946 A | 2/1998 | Ben-Haim |
| 5,749,362 A | 5/1998 | Funda et al. |
| 5,859,934 A | 1/1999 | Green |
| 5,876,325 A | 3/1999 | Mizuno et al. |
| 5,951,475 A | 9/1999 | Gueziec et al. |
| 6,226,543 B1 | 5/2001 | Gilboa et al. |
| 6,259,806 B1 | 7/2001 | Green |
| 6,272,371 B1 | 8/2001 | Shlomo |
| 6,424,885 B1 | 7/2002 | Niemeyer et al. |
| 6,551,281 B1 | 4/2003 | Raulerson et al. |
| 6,726,675 B1 | 4/2004 | Beyar |

(Continued)

FOREIGN PATENT DOCUMENTS

| CN | 102151134 A | 8/2011 |
| CN | 202044271 U | 11/2011 |

(Continued)

*Primary Examiner* — Sean Dougherty
(74) *Attorney, Agent, or Firm* — Dorsey & Whitney LLP

(57) ABSTRACT

A device may operate a guide wire and be operable by a single operator digit. The device may include an insertion control device for advancing the guide wire in a forward and in a reverse direction and along a longitudinal axis of the guide wire; and a rotary device for rolling a guide wire about the longitudinal axis. A robotic instrument driver may be operatively coupled to the device and configured to control axial movement of the guide wire along the longitudinal axis according to input received from the insertion control device and to control rotational movement of the guide wire according to input received from the rotary device.

14 Claims, 5 Drawing Sheets

(56) References Cited

U.S. PATENT DOCUMENTS

| | | | |
|---|---|---|---|
| 7,155,315 B2 | 12/2006 | Niemeyer et al. | |
| 2006/0025676 A1 | 2/2006 | Viswanathan et al. | |
| 2006/0190034 A1 | 8/2006 | Nishizawa et al. | |
| 2008/0097465 A1* | 4/2008 | Rollins et al. | 606/108 |
| 2010/0057045 A1 | 3/2010 | Albritton, IV et al. | |
| 2010/0204613 A1* | 8/2010 | Rollins et al. | 600/585 |
| 2012/0075638 A1* | 3/2012 | Rollins et al. | 356/479 |
| 2015/0105747 A1* | 4/2015 | Rollins et al. | 604/500 |

FOREIGN PATENT DOCUMENTS

| | | | | |
|---|---|---|---|---|
| JP | 07225343 A | 8/1995 | | |
| WO | 03086190 A1 | 10/2003 | | |
| WO | WO 2008049088 A2 * | 4/2008 | | A61M 25/09 |

* cited by examiner

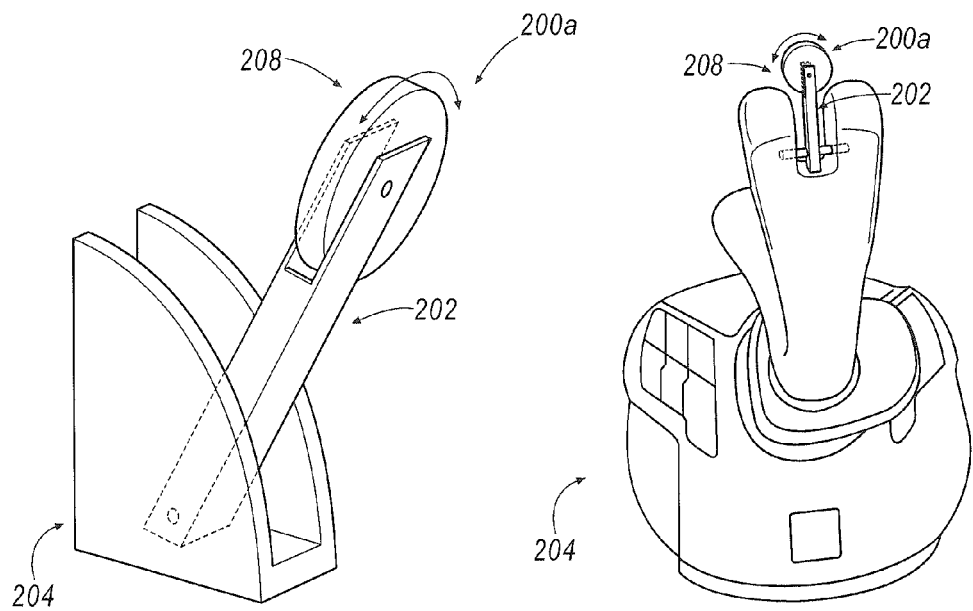
FIG. 2A
FIG. 2D
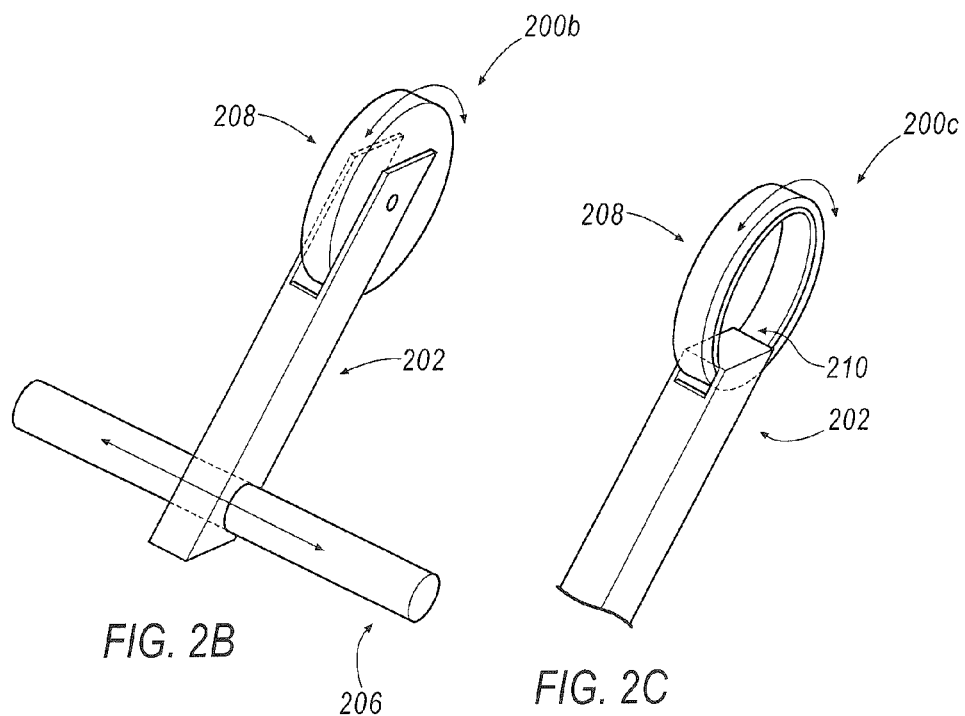
FIG. 2B
FIG. 2C

INTEGRATED CATHETER AND GUIDE WIRE CONTROLLER

BACKGROUND

Minimally invasive surgery (MIS) systems may utilize flexible robotic catheters that are navigated in the bloodstream of a patient and visualized using X-rays. MIS apparatus and techniques have advanced to the point where an elongated catheter instrument is controllable by selectively operating tensioning control elements within the catheter instrument. In one example, four opposing directional control elements wend their way to the distal end of the catheter which, when selectively placed in and out of tension, cause the distal end to steerably maneuver within the patient. Control motors are coupled to each of the directional control elements so that they may be individually controlled and the steering effectuated via the operation of the motors in unison.

A controller device includes an assortment of controls to allow an operator to maneuver the catheter instrument as well as a guide wire guided by the catheter instrument. Some controller devices employ buttons dedicated to control the catheter instrument and a second set of buttons to control the guide wire. Other controller devices include a joystick type controller to control the catheter, often one-handed, and a separate set of button controls to control the guide wire. For instance, gross hand motion of a joystick may be used to control the catheter, leaving the operator to use one's thumb and fine finger control to manipulate the guide wire. When controlling such catheter devices, coordinated motion of the catheter device and guide wire may be difficult to perform. Thus, such systems may lack the precision desired by operators of the robotic catheter system for performing MIS operations.

SUMMARY

An exemplary device for operating a guide wire may include an insertion control device for advancing the guide wire in a forward and reverse direction along a longitudinal axis of the guide wire; and a rotary device for rolling a guide wire about the longitudinal axis; wherein the device is operable by a single operator digit, allowing the rest of the operator hand to control a catheter.

An exemplary system may include a guide wire control device operable by a single operator digit and including an insertion control device for advancing a guide wire in a forward and reverse direction along a longitudinal axis of the guide wire, and a rotary device for rolling a guide wire about the longitudinal axis. The system may further include a robotic instrument driver operatively coupled to the guide wire control device and configured to control axial movement of the guide wire along the longitudinal axis according to input received from the insertion control device and to control rotational movement of the guide wire according to input received from the rotary device.

BRIEF DESCRIPTION OF THE DRAWINGS

FIG. 2A illustrates an exemplary device having a pivotable insertion control member onto which a vertical rotary control is mounted;

FIG. 2B illustrates an exemplary device having a slidable insertion control member onto which a vertical rotary control is mounted;

FIG. 2C illustrates an exemplary rotary control having a digit rest suitable for use with the exemplary devices of FIGS. 2A and 2B;

FIG. 2D illustrates an exemplary device mounted to a control member of a joystick;

DETAILED DESCRIPTION

Figure 1:
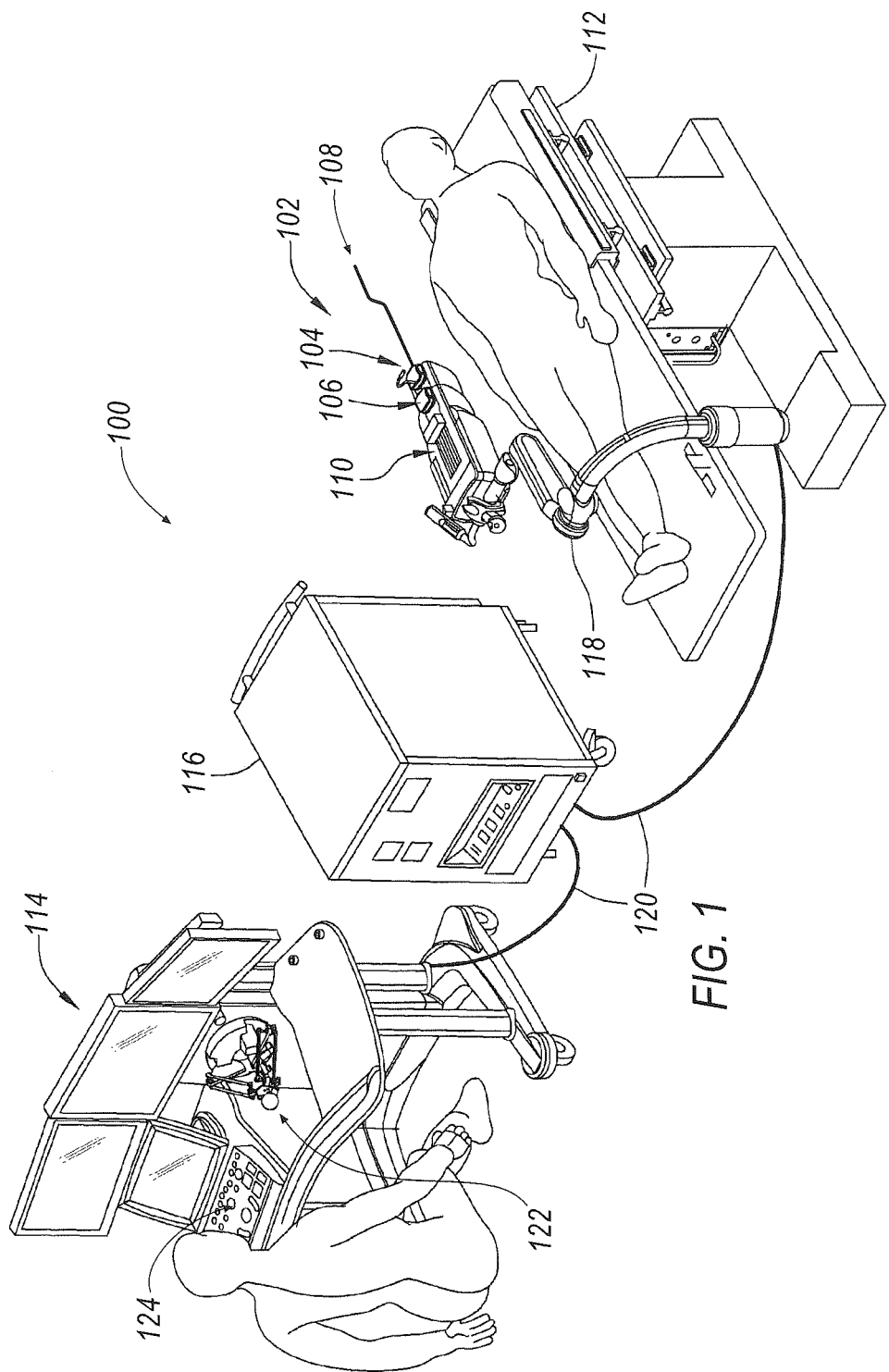
FIG. 1 illustrates an exemplary robotically controlled surgical system.

Referring to FIG. 1, a robotically controlled surgical system 100 is illustrated in which an apparatus, a system, and/or method may be implemented according to various exemplary illustrations. System 100 may include a robotic catheter assembly 102 having a robotic or first or outer steerable complement, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter 106" or "catheter instrument 106"). The catheter instrument 106 may further include a guide wire 108 extendable beyond a distal end of the catheter instrument 106. Catheter assembly 102 is controllable using a robotic instrument driver 110 (generally referred to as "instrument driver"). During use, a patient is positioned on an operating table or surgical bed 112 (generally referred to as "operating table") to which robotic instrument driver 110 is coupled or mounted. In the illustrated example, system 100 includes an operator workstation 114, an electronics rack 116 and associated bedside electronics box (not shown), a setup joint mounting brace 118, and instrument driver 110. A surgeon is seated at operator workstation 114 and can monitor the surgical procedure, patient vitals, and control one or more catheter devices.

System components may be coupled together via a plurality of cables or other suitable connectors 120 to provide for data communication, or one or more components may be equipped with wireless communication components to reduce or eliminate cables 120. Communication between components may also be implemented over a network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

The operator workstation 114 may include a computer monitor configured to display a three dimensional object, such as a representation of the catheter instrument 106 and guide wire 108. The catheter instrument 106 and guide wire 108 may be displayed within or relative to a three dimensional space, such as a body cavity or organ, e.g., a chamber of a patient's heart.

The operator workstation 114 may further provide for control of the catheter 106 and guide wire 108. As one example, the operator workstation 114 may include a set of controls having a joystick type controller 122 and a keyboard type input device 124. The catheter 106 may be controlled using the joystick type controller 122 allowing for steering of the distal tip of the guide catheter 106 as viewed on the computer monitor display, while the guide wire 108 may be controlled using the keyboard type input device 124.

The joystick type controller 122 may further include various sensors to detect the position of the joystick type controller 122 and to provide signals to the controller that are interpreted as commands. The joystick type controller 122 may also include a control member configured to move about a pivot point along one or more axes. In some cases, additional controls such as buttons may be positioned on the control member or a base of the joystick type controller 122.

A variation of the keyboard type input device 124 of FIG. 1 may include controls for the sheath catheter and elongate member manipulator. The keyboard type input device 124 may include bend, insert and rotate controls to steer the sheath catheter, as well as rotate and insert controls to control the elongate member manipulator. In alternative variations, the distal tip of the guide wire 108 may be controlled using the joystick type controller 122 while the guide and sheath catheters may be controlled by the keyboard type input device 124.

However, controlling coordinated motion of the catheter 106 and guide wire 108 using the joystick type controller 122 in combination with the keyboard type input device 124 may be difficult for operators to perform. For example, to perform a spiraling motion for breaking friction in wire control, the operator may be required to perform precise actions with the joystick type controller 122 in one hand, and the keyboard type input device 124 in the other hand.

A device may be designed that allows for simultaneous guide wire 108 roll and guide wire 108 insertion operated by a single digit of the operator, allowing the rest of the operator hand to control a catheter 106. The digit may include the thumb or any of the four fingers of a hand. The device may be placed on a control member of the catheter control joystick 122, and may be utilized to provide for both rotational control of the guide wire 108 according to a rotary device and also axial control of the guide wire 108 device (e.g., insert, retract) by way of a separate but readily reachable insertion/retraction control aspect of the device. Various thumb and fine-finger devices such as rotational wheels and trackballs may be utilized as the rotary device in combination with guide wire 108 insertion control to provide for advanced command control features such as simultaneous roll and insertion of a guide wire 108, without requiring the operator to work with a second set of guide wire 108 or other controls.

FIG. 2A illustrates an exemplary device 200-A having a pivotable insertion control member 202 onto which a vertical rotary control 208 is mounted. By providing for guide wire 108 insertion control using the insertion control member 202 and also guide wire 108 roll control using the vertical rotary control 208, the device 200 may facilitate single-digit performance of a spiraling insertion motion for breaking friction during wire control.

More specifically, a first end of the insertion control member 202 may be connected to a base member 204, such as by way of a pivot pin, bolt or hinge, thereby providing for forward and back pivoting motion of the insertion control member 202 about an axis of rotation. Tilt of the insertion control member 202 may be measured by way of a potentiometer or Hall Effect sensors mounted to turn along the pivot point, or switches mounted to the base member 204 that are selectively engaged and disengaged due to the pivoting movement of the insertion control member 202. Forward motion of the insertion control member 202 about the axis of rotation may be detected by the sensors, and provide for insertion control of a guide wire 108, while backward motion of the insertion control member 202 about the axis of rotation may also be detected by the sensors and may provide for retraction control (or a reverse control configuration). In some examples, a spring return or other biasing mechanism may further be included to center the insertion control member 202 to a midpoint or other intermediate point along its axis of rotation.

Since the pivot range of the insertion control member 202 may be relatively limited as compared to the insertion range of the guide wire 108, control of insert and retract may be performed according to velocity control, wherein the insertion control member 202 controls the velocity of the guide wire 108 insertion and retraction as opposed to direction or speed. Velocity may be calculated, for example, by comparing a current position of the insertion control member 202 in a current measurement cycle to the position of the insertion control member 202 in a previous measurement cycle. A maximum velocity limit may be used to cap the determined velocity to be within a predefined velocity limit. The predefined velocity limit may be related to factors such as a maximum speed of insertion or retraction capable of being performed by the system 100 or a safety threshold to protect the patient from high-velocity guide wire 108 movements.

The vertical rotary control 208 may be mounted vertically at a second end of the insertion control member 202, such that the vertical rotary control 208 may be free to rotate perpendicular to the axis of rotation of the insertion control member 202. The vertical rotary control 208 may be configured to measure an operator-applied rotation, such as by use of an infinite roll encoder, potentiometer or other rotational sensor, as some examples, and to apply the provided rotation to the guide wire 108. The vertical rotary control 208 may provide for an absolute position control mode (e.g., wherein a controlled drive mechanism follows the movements of the vertical rotary control 208), or a relative position control mode (e.g., in which rotation of the vertical rotary control 208 provides for a corresponding amount of roll of the guide wire 108 when the vertical rotary control 208 is in an active or clutched state but not when in an inactive or released clutch state).

For the roll component of the control, relative or absolute position control may be applicable modes of control because the guide wire 108 may experience whip, and in order to understand that whip is happening, an operator of the user interface device 200 may need to connect visual feedback with respect to actual wire roll (e.g., by using fluoroscope imaging displayed on the computer monitor display of the of the operator workstation 114) with an expected amount that the operator is turning the vertical rotary control 208. For instance, if the operator of the user interface device 200 has turned the vertical rotary control 208 by a full turn and the operator does not see movement in the guide wire 108 tip, the operator may infer that wind-up is occurring and that further rolling of the guide wire 108 should be avoided.

FIG. 2B illustrates an alternate exemplary device 200-B having a slidable insertion control member 202 onto which the vertical rotary control 208 is mounted. Thus, rather than providing bi-directional guide wire 108 insertion control by pivoting about a point as done in the exemplary device 200-A, in the exemplary device 200-B the insertion control member 202 may be positioned on a slider that slides backwards and forwards in a linear motion along an axis.

Exemplary slider implementations may include tongue-in-groove attachments or other suitable couplings facilitating movement of the insertion control member 202 along an articulation path 206. The path 206 may be supported in various ways, such as by one or more end supports holding the path 206 in place to a base member 204. Location of the insertion control member 202 along the slide may be measured in various ways, such as according to a connection of the insertion control member 202 to a linear potentiometer or other sensor attached to the slide, as one example. Forward motion of the insertion control member 202 along the articulation path 206 may therefore provide for sensed insertion control of a guide wire 108, while backward motion of the insertion control member 202 along the articulation path 206 may provide for sensed retraction control (or a reverse control configuration). As with the pivotable insertion control member 202 of device 200-A, the slidable insertion control member 202 of device 200-B may include a biasing mechanism to center the insertion control member 202 to a midpoint or other point along its slidable axis.

The slidable insertion control member 202 may operate in a variety of control modes, such as in a position control mode or in a velocity control mode. As a further example, the slidable insertion control member 202 may operate in a combination control mode in which the position control mode may be utilized in the center range of the articulation path 206 of the slider and the velocity control mode may be utilized near the ends of the articulation path 206 range.

FIG. 2C illustrates an alternate exemplary vertical rotary control 208 having a digit rest 210 suitable for use with the exemplary devices of FIGS. 2A and 2B. The exemplary vertical rotary control 208 may include a digit rest 210 formed by way of a hollow ring or other opening, such that a thumb or other digit of a hand of an operator may pass through. An outer ring vertical rotary control 208 may surround the digit rest 210 and may measure an operator-applied rotation, such as by use of an infinite roll encoder, potentiometer or other rotational sensor, as some examples. Another digit of the hand, such as an index finger, may engage the outside surface of the outer ring vertical rotary control 208, such that the operator may apply the rotational motion to the ring vertical rotary control 208. The alternate exemplary vertical rotary control 208 may accordingly provide for full rotation of the wheel by the operator, while still allowing for insert and retraction control by way of the pivotable or slideable insertion control members 202 described in detail above.

FIG. 2D illustrates an exemplary device 200-A mounted to a control member of a joystick 122. As illustrated, the device 200-A may be utilized to provide for both rotational control of the guide wire 108 according to the rotary device 208 and also axial control of the guide wire 108 device (e.g., insert, retract) by movement of the control member 202. Control of the catheter may also be performed according to the catheter control functions of the joystick device 122. While the device 200-A is illustrated, it should be noted that other guide wire 108 control devices, including any of the exemplary devices 200 or 300 discussed herein, may similarly be mounted to the joystick 122 control member.

Figure 3A:
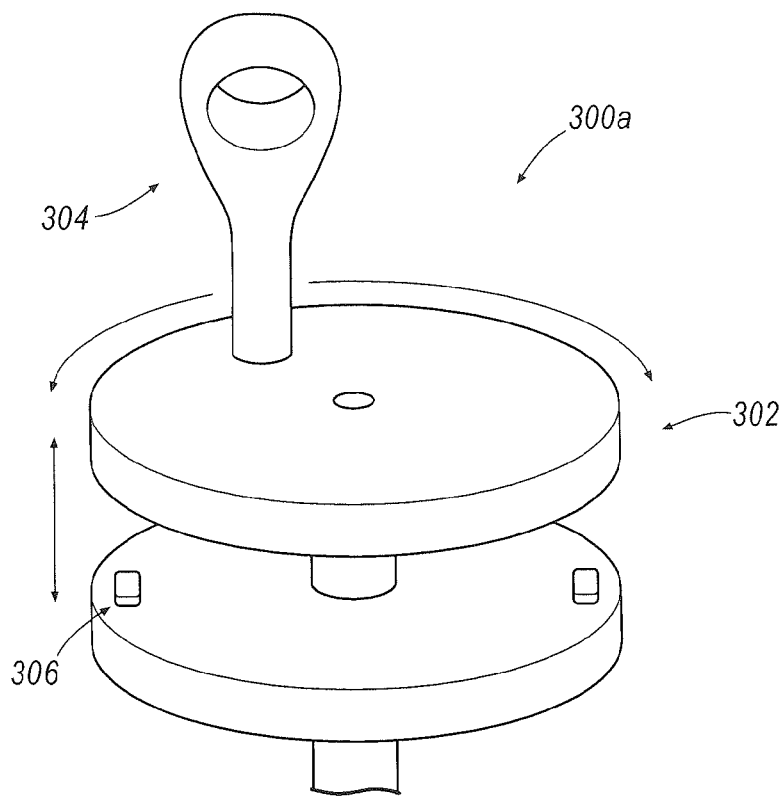
FIG. 3A illustrates an exemplary device including a horizontal rotary control and a digit rest.

FIG. 3A illustrates an exemplary device 300-A including a horizontal rotary control 302 and digit holder 304. As with the device 200, the device 300 may also provide for rotational control of the guide wire 108 as well as bidirectional insertion control of the guide wire 108, performed according to a separate motion of the device 300 in combination with the rotary control.

In the exemplary device 300-A, an axle or other support may be fixed to a base member at a first end, and to a horizontal rotary control 302 at the second end. The horizontal rotary control 302 may include a wheel attached to the support at or near the second end of the base member, such that the wheel may be free to rotate about the support on an axis of rotation extending along the axis of the support. The support may further include a groove or other slide path allowing the wheel to translate a distance along axis of rotation. The horizontal rotary control 302 may further include a second wheel or other surface onto which one or more switches 306 or other sensors 306 facing the first wheel may be mounted. The sensors 306 may be capable of detecting translation movement of the wheel along the axis of rotation, such as according to switches having selective mechanical engagement with the first wheel, or a type of proximity sensor 306 such as an infrared, capacitive, or inductive sensor 306. In some examples, translation of the first wheel toward the sensors 306 may provide for insertion control, while translation of the first wheel in an opposite direction away from the switches may provide for retraction control.

A first end of a thumb holder axle or other support member may be affixed to the top face of the first wheel, on the side opposite the wheel support, and at a location offset from the center of the first wheel. The digit holder 304 may be connected to the digit holder support such that the digit holder 304 may freely rotate about the axis of the support. The digit holder 304 may be formed by way of a hollow ring or other opening such that a digit may pass into and rest within the enclosed space. An operator may insert a digit into the digit holder 304 and may use the digit holder 304 to rotationally drive the first wheel of the horizontal rotary control 302 such that the digit may remain in substantially the same orientation throughout the rotation. Moreover, due to the digit holder 304 encircling the operator digit, the operator may push or pull the digit holder 304 along the axis of rotation, thereby pushing or pulling the horizontal rotary control 302, in turn causing the sensors 306 to detect the translation and provide for guide wire 108 insertion control. The horizontal rotary control 302 may further include a biasing mechanism to center the first wheel to a midpoint along its slidable axis.

Figure 3B:
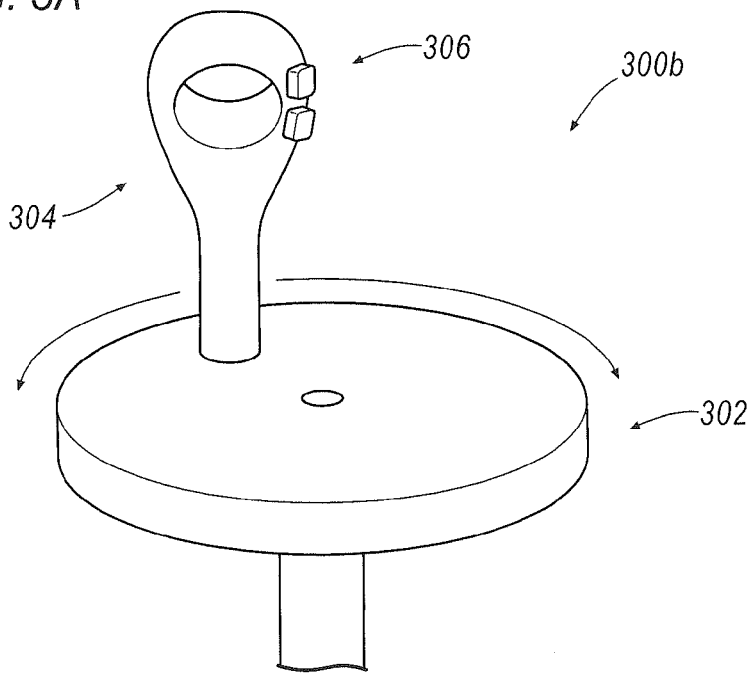
FIG. 3B illustrates an alternate exemplary device including a horizontal rotary control and a digit rest including insert and retract buttons.

FIG. 3B illustrates an alternate exemplary device 300-B including a horizontal rotary control 302 and a digit holder 304 including insert and retract buttons. As with the device 300-A, the device 300-B may provide for rotational control of the guide wire 108 according to a horizontal rotary control 302 having a digit holder 304. However, instead of providing bidirectional insertion control of the guide wire 108 according to translation of the horizontal rotary control 302, the device 300-B instead includes guide wire controls 306 (e.g., an insert button and a retract button) mounted on an exterior surface of the digit holder 304. Accordingly, an operator may insert a digit into the digit holder 304 to rotationally drive the horizontal rotary control 302, and may use another digit to press the insert button and retract buttons to provide for guide wire 108 insertion control. For instance, the operator may insert a thumb into the digit holder 304, and may utilize the insert button and retract buttons using an index finger in a pinching motion.

Figure 3C:
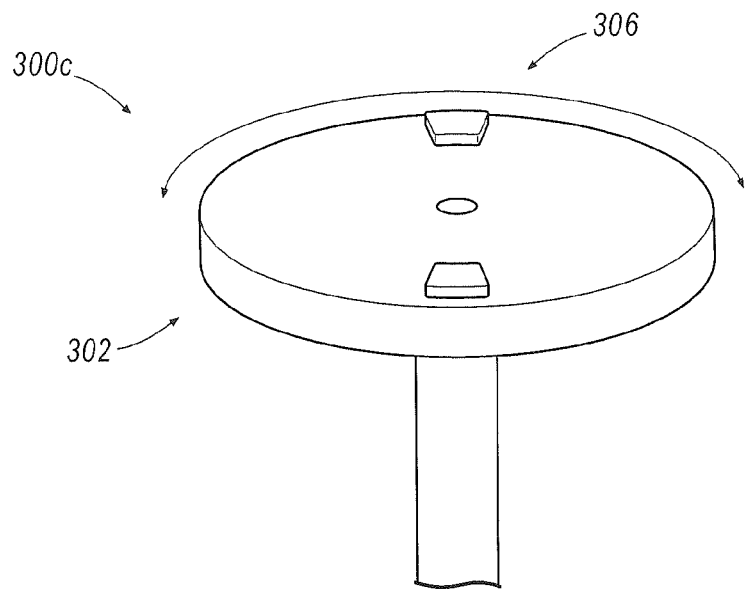
FIG. 3C illustrates an alternate exemplary device including a horizontal rotary control and insert and retract buttons.

FIG. 3C illustrates an alternate exemplary device 300-C including a horizontal rotary control 302 and insert and retract buttons. As with the devices 300-A and 300-B, the device 300-B may provide for rotational control of the guide wire 108 according to a horizontal rotary control 302. To provide for guide wire 108 insertion control, guide wire controls 306 such as an insert button and a retract button may be mounted on the horizontal rotary control 302 on the top surface opposite the support. To facilitate use of the insert button and a retract button for guide wire 108 insertion control, the buttons may be visibly marked as being assigned to the insert or retract functions. Moreover, to allow for control of guide wire 108 insertion while looking elsewhere than the face of the horizontal rotary control 302 (e.g., viewing an insertion site, viewing a fluoroscope or computer monitor display of the operator workstation 114, etc.), the insert button and retract button may further be distinguishable according to tactile feel (e.g., by way of use of different button shapes, or different patterns of raised dots or other textured identification differing between the inset and retract buttons). In some examples, the insert button and retract button may be arranged opposite of one other on the face of the horizontal rotary control 302, while in other examples, the insert button and retract button may be arranged to be relatively adjacent to one another.

Figure 3D:
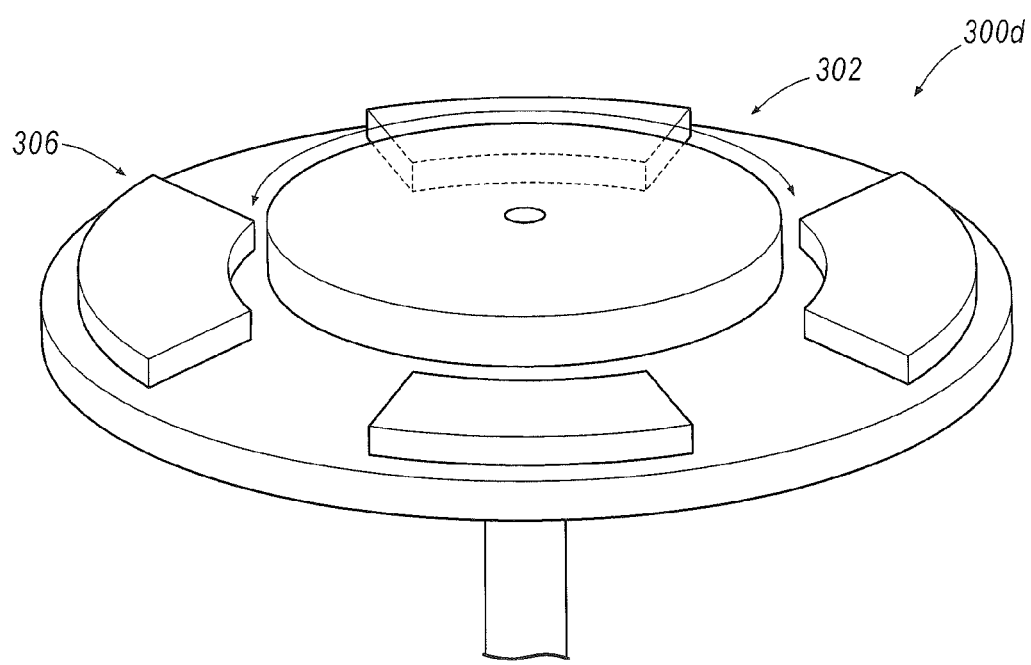
FIG. 3D illustrates an alternate exemplary device including a horizontal rotary control and a directional pad for catheter control.

FIG. 3D illustrates an alternate exemplary device 300-D including a horizontal rotary control 302 and directional pad guide wire control sensors 306. As with the device 300-A through 300-C, the device 300-D may provide for rotational control of the guide wire 108 according to a horizontal rotary control 302. However, to provide for guide wire 108 insertion control, rather than using buttons that rotate with the horizontal rotary control 302 as described with respect to the device 300-C, the device 300-D may include directional pad guide wire control sensors 306 mounted about the horizontal rotary control 302. In some cases the directional pad guide wire control sensors 306 may be mounted to the support for the horizontal rotary control 302, while in other cases the horizontal rotary control 302 may be mounted to the directional pad guide wire control sensors 306 instead. The (typically) four buttons of the directional pad guide wire control sensors 306 may be mapped to various guide wire 108 control functions. As one example, an "up" directional pad guide wire control sensor 306 may be mapped to insert, a "down" sensor 306 to retract, and "left" and "right" sensors 306 to opposite directions of articulation of the guide wire 108.

Figure 4A:
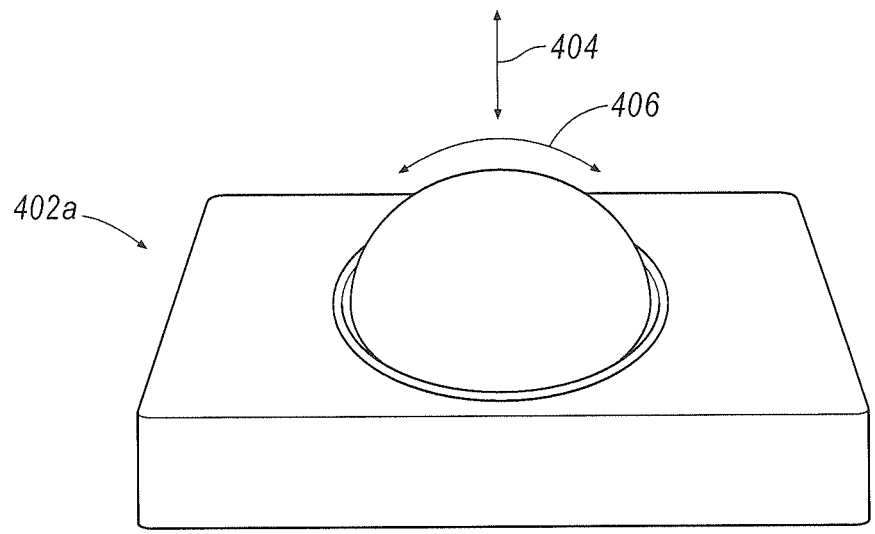
FIG. 4A illustrates an exemplary device including a trackball control.

FIG. 4A illustrates an exemplary trackball control 402-A. A trackball control 402 may be any of various devices including a ball element held by a socket, the socket containing sensors to detect a rotation of the ball about two axes. An exemplary trackball control 402 may be of a small size, such as one centimeter in diameter, to provide for easy control of both axes. However, trackballs of larger or smaller diameters may be utilized as well. To measure the rotation of the trackball, the trackball control 402 may include wheels in contact with the trackball in orthogonal directions (i.e., for X and Y axes of rotation). Optical or Hall Effect sensors may be coupled to the contact wheels to derive positioning information from the movement of the wheels against the trackball. Motion of the trackball control 402 about the Y-axis 404 may be mapped to the guide wire 108 insert and retract function, while motion in the X direction 406 may be mapped to guide wire 108 roll.

Because trackball control 402 motion may be infinite in both X and Y axes, the trackball control 402 may be suitable for relative position control in insert and retract. In some examples, to facilitate operator input of fast motions, the insert direction may include an inertia control such that once a certain degree of rotation in the insert Y-axis direction in achieved, the trackball control 402 may transition to the velocity control mode as discussed above. Thus, once in the velocity control mode, the guide wire 108 may continue to insert until the operator moves the trackball again (e.g., in a direction corresponding to retract), thereby reducing the velocity or exiting velocity control mode and returning the exemplary trackball control 402 to a non-velocity control mode of control.

Figure 4B:
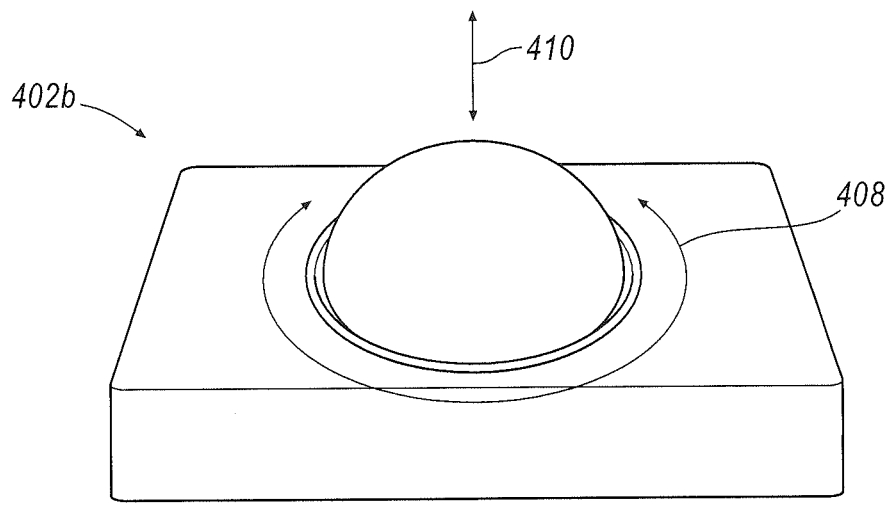
FIG. 4B illustrates an alternate exemplary device including a trackball control.

As another possibility, as shown in FIG. 4B, another control scheme using the trackball control 402 may include use of the circular direction of the trackball 408 as roll and radial movement of the trackball 410 as performing insertion and retraction motions. As yet a further possibility the track ball concept could be applied to a touchpad, where swipe gestures in an X-axis may provide roll positioning and swipe gesture in a Y-axis may provide for positioning.

Thus, a device, such as the devices 200-400 discussed in detail above, may be mounted to a control member of a joystick 122 and may be designed to allow for simultaneous guide wire 108 roll and guide wire 108 insertion controlled by a single digit of an operator hand, allowing the rest of the operator hand to control a catheter 106. By providing rotational control of the guide wire 108 according to a rotary control device and also axial control of the guide wire 108 (e.g., insert, retract) according to an insertion control, the device may provide for single-digit control of features such as simultaneous roll and insertion of a guide wire 108, without requiring the operator to work with a second set of guide wire 108 or other controls in another hand.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein. The software executed by the operator workstation 114 may be one such computer program product. In some example, the operator workstation 114 software when executed by one or more processors may provide the operations described herein. Alternatively, the software may be provided as hardware or firmware, or combinations of software, hardware and/or firmware.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A system for manipulating a guide wire, the system comprising:
   an instrument driver coupled to a guide wire; and
   an operator workstation communicatively coupled to, but physically remote from, the instrument driver and the guide wire, wherein the operator workstation is configured to receive control inputs from an operator and comprises a guide wire control device, wherein the guide wire control device comprises:
      an insertion control member for controlling advancement and retraction of the guide wire along a longitudinal axis of the guide wire; and
      a rotary member for controlling roll of the guide wire about the longitudinal axis,
      wherein a first end of the insertion control member is movably coupled to a base member and a second end of the insertion control member is coupled to the rotary member, such that the rotary member is free to rotate relative to the insertion control member, and
      wherein the guide wire control device is configured to receive the control inputs from the operator by a single operator digit.

2. The system of claim 1, wherein the insertion control member is movable within a range of controlled motion along a first axis of the insertion control member, and wherein the guide wire control device further comprises an insertion control sensor configured to measure the motion along the first axis to provide commands for control of the guide wire along the longitudinal axis.

3. The system of claim 2, wherein the rotary member is vertically mounted to the second end of the insertion control member and is configured to rotate perpendicular to the first axis of the insertion control member, and wherein the guide wire control device further comprises a rotation control sensor configured to measure rotation of the rotary member to provide commands for rolling the guide wire.

4. The system of claim 1, wherein the insertion control member is at least one of pivotably mounted or slidably mounted at the first end to the base member.

5. The system of claim 2, wherein the insertion control member operates in a position control mode in a center range of the controlled motion along the first axis and in a velocity control mode in a range outside the center range of the controlled motion along the first axis.

6. The system of claim 1, wherein the instrument driver is robotic, operatively coupled to the guide wire control device, and configured to impart axial movement of the guide wire along the longitudinal axis according to an input received from the insertion control member and to impart rotational movement of the guide wire according to an input received from the rotary member.

7. The system of claim 1, wherein the rotary member is configured to operate in a control mode, including at least one of:
   an absolute position control mode, in which the guide wire follows movements of the rotary member to provide a corresponding amount of roll to the guide wire, or
   a relative position control mode, in which rotation of the rotary member provides a corresponding amount of roll to the guide wire when the rotary member is in an active clutched state but not when in an inactive released-clutch state.

8. The system of claim 1, further comprising a digit rest having an opening that the single operator digit may pass through, wherein the rotary member includes a rotating ring surrounding the digit rest.

9. The system of claim 1, wherein the rotary member is horizontally mounted to a vertical support member on an axis of rotation extending along an axis of the vertical support member, and further comprising a digit holder attached to a top face of the rotary member by a digit holder support at a location offset from a center of the rotary member, such that the digit holder may freely rotate about an axis of the digit holder support.

10. The system of claim 9, further comprising:
    an insertion control mounted to the digit holder and configured to provide commands for axial insertion control of the guide wire; and
    a retraction insertion control mounted to the digit holder and configured to provide commands for axial retraction control of the guide wire.

11. The system of claim 9, wherein the vertical support member includes a slide path allowing the rotary member to translate a distance along the axis of rotation, wherein the guide wire control device includes at least one sensor capable of detecting translation movement of the rotary member along the axis of rotation to provide commands for axial control of the guide wire.

12. A system, comprising:
    a robotic instrument driver coupled to a guide wire;
    an operator workstation communicatively coupled to, but physically remote from, the instrument driver and the guide wire, wherein the operator workstation is configured to receive control inputs from an operator and comprises a guide wire control device operable by a single operator digit, the guide wire control device comprising:
       an insertion control member for controlling advancement of the guide wire in a forward direction and a reverse direction along a longitudinal axis of the guide wire; and a rotary member for controlling roll of the guide wire about the longitudinal axis; and a catheter controller, wherein the guide wire control device is mounted to the catheter controller, wherein the instrument driver is configured to impart axial movement to the guide wire along the longitudinal axis according to an input received from the insertion control member and to impart rotational movement to the guide wire according to an input received from the rotary member.

13. The system of claim 12, wherein the input from the insertion control member and the input from the rotary member are received from an operator substantially simultaneously, and wherein imparting the axial movement to the guide wire along the longitudinal axis and the rotational movement to the guide wire are performed substantially simultaneously and in response to the received inputs.

14. The system of claim 12, wherein the catheter controller comprises a joystick control configured to move about a pivot point.

* * * * *